United States Patent
Bhattacharya et al.

(10) Patent No.: US 11,547,484 B2
(45) Date of Patent: Jan. 10, 2023

(54) SELECTION OF INTRAOCULAR LENS BASED ON A PLURALITY OF MACHINE LEARNING MODELS

(71) Applicant: Alcon Inc., Fribourg (CH)

(72) Inventors: Sinchan Bhattacharya, Denton, TX (US); Ramesh Sarangapani, Coppell, TX (US)

(73) Assignee: Alcon Inc., Fribourg (CH)

( * ) Notice: Subject to any disclaimer, the term of this patent is extended or adjusted under 35 U.S.C. 154(b) by 282 days.

(21) Appl. No.: 17/064,254

(22) Filed: Oct. 6, 2020

(65) Prior Publication Data
US 2021/0106385 A1 Apr. 15, 2021

Related U.S. Application Data

(60) Provisional application No. 62/912,682, filed on Oct. 9, 2019.

(51) Int. Cl.
| | |
|---|---|
| A61B 34/10 | (2016.01) |
| G06T 7/62 | (2017.01) |
| G06T 7/70 | (2017.01) |
| G16H 20/40 | (2018.01) |
| G16H 30/20 | (2018.01) |
| G16H 50/30 | (2018.01) |
| G16H 50/70 | (2018.01) |
| G16H 50/20 | (2018.01) |
| G16H 30/40 | (2018.01) |

(Continued)

(52) U.S. Cl.
CPC ............... *A61B 34/10* (2016.02); *A61B 8/10* (2013.01); *A61F 2/16* (2013.01); *G06T 7/62* (2017.01); *G06T 7/70* (2017.01); *G16H 20/40* (2018.01); *G16H 30/20* (2018.01); *G16H 30/40* (2018.01); *G16H 50/20* (2018.01); *G16H 50/30* (2018.01); *G16H 50/70* (2018.01); *A61B 2034/108* (2016.02); *G06T 2207/10132* (2013.01); *G06T 2207/20081* (2013.01); *G06T 2207/30041* (2013.01); *G06T 2207/30052* (2013.01)

(58) Field of Classification Search
CPC ..... A61B 2034/108; A61B 34/10; A61B 8/10; G06T 2207/10132; G06T 2207/20081; G06T 2207/30041; G06T 2207/30052; G06T 7/62; G06T 7/70; A61F 2/16; G16H 20/40; G16H 30/20; G16H 30/40; G16H 50/20; G16H 50/30; G16H 50/70
See application file for complete search history.

(56) References Cited

U.S. PATENT DOCUMENTS

2019/0209242 A1* 7/2019 Padrick .................. G16H 20/40

* cited by examiner

*Primary Examiner* — Manuchehr Rahmjoo

(57) ABSTRACT

A method and system for selecting an intraocular lens, with a controller having a processor and tangible, non-transitory memory. A plurality of machine learning models is selectively executable by the controller. The controller is configured to receive at least one pre-operative image of the eye and extract, via a first input machine learning model, a first set of data. The controller is configured to receive multiple biometric parameters of the eye and extract, via a second input machine learning model, a second set of data. The first set of data and the second set of data are combined to produce a mixed set of data. The controller is configured to generate, via an output machine learning model, at least one output factor based on the mixed set of data. An intraocular lens is selected based in part on the at least one output factor.

18 Claims, 4 Drawing Sheets

(51) Int. Cl.
*A61B 8/10* (2006.01)
*A61F 2/16* (2006.01)

SELECTION OF INTRAOCULAR LENS BASED ON A PLURALITY OF MACHINE LEARNING MODELS

INTRODUCTION

The disclosure relates generally to a system and method of selecting an intraocular lens for implantation in an eye, using a plurality of machine learning models. The human lens is generally transparent such that light may travel through it with ease. However, many factors may cause areas in the lens to become cloudy and dense, and thus negatively impact vision quality. The situation may be remedied via a cataract procedure, whereby an artificial lens is selected for implantation into a patient's eye. Indeed, cataract surgery is a common surgery performed all around the world. An important driver of clinical outcome for cataract surgery is the selection of an appropriate intraocular lens. Currently, there are several calculators that use various pre-operative information regarding the patient's eye to predict the lens power to be implanted. However, the existing calculators do not use the full pre-operative image of the eye as input data.

SUMMARY

Disclosed herein is a system and method of selecting an intraocular lens for implantation in an eye, with a controller having a processor and tangible, non-transitory memory. The system employs a comprehensive, multi-prong approach and includes a controller having a processor and tangible, non-transitory memory on which instructions are recorded. The controller is configured to selectively execute a plurality of machine learning models, including a first input machine learning model, a second input machine learning model and an output machine learning model. Each of the plurality of machine learning models may be a respective regression model. In one example, the output machine learning model includes a multi-layer perceptron network.

Execution of the instructions by the processor causes the controller to receive at least one pre-operative image of the eye. The controller is configured to extract, via the first input machine learning model, a first set of data based in part on the at least one pre-operative image. In one example, the at least one pre-operative image of the eye is an ultrasound bio-microscopy image. The first set of data may include a plurality of pre-operative dimensions of the eye. The plurality of pre-operative dimensions may include one or more of an anterior chamber depth, a lens thickness, a lens diameter, a sulcus-to-sulcus diameter, a first equatorial plane position, a second equatorial plane position, a third equatorial plane position, an iris diameter, an axial length from a first surface of a cornea to a posterior surface of a pre-operative lens and a ciliary process diameter. Alternatively, the plurality of pre-operative dimensions may include each of the anterior chamber depth, lens thickness, lens diameter, sulcus-to-sulcus diameter, iris diameter, axial length from the first surface of the cornea to the posterior surface of the pre-operative lens and the ciliary process diameter.

The controller is further configured to receive multiple biometric parameters of the eye and extract, via the second input machine learning model, a second set of data based in part on the multiple biometric parameters. The multiple biometric parameters may include a K flat factor and a K steep factor. The first set of data and the second set of data are combined to obtain a mixed set of data. In one example, the pre-operative image is obtained from a first imaging device and the multiple biometric parameters are obtained from a second imaging device, the second imaging device being different from the first imaging device. For example, the first imaging device may be an ultrasound device and the second imaging device may be an optical coherence tomography device.

The controller is configured to generate, via the output machine learning model, at least one output factor based on the mixed set of data. The intraocular lens is selected based in part on the output factor. The output factor may be a manifest refraction spherical equivalent (MRSE). The plurality of machine learning models may include a third input machine learning model. Prior to generating the output factor, the controller may be configured to access historical pairs of respective pre-operative and post-operative images and extract, via the third input machine learning model, a third set of data based in part on the historical pairs. The third set of data is added to the mixed set of data prior to generating the output factor.

The intraocular lens may include an optic zone contiguous with one or more supporting structures. The intraocular lens may include an internal cavity at least partially filled with a fluid. The fluid is configured to move within the internal cavity to vary a power of the intraocular lens. It is understood that any type of intraocular lens available to those skilled in the art may be employed.

The above features and advantages and other features and advantages of the present disclosure are readily apparent from the following detailed description of the best modes for carrying out the disclosure when taken in connection with the accompanying drawings.

DETAILED DESCRIPTION

Figure 1:
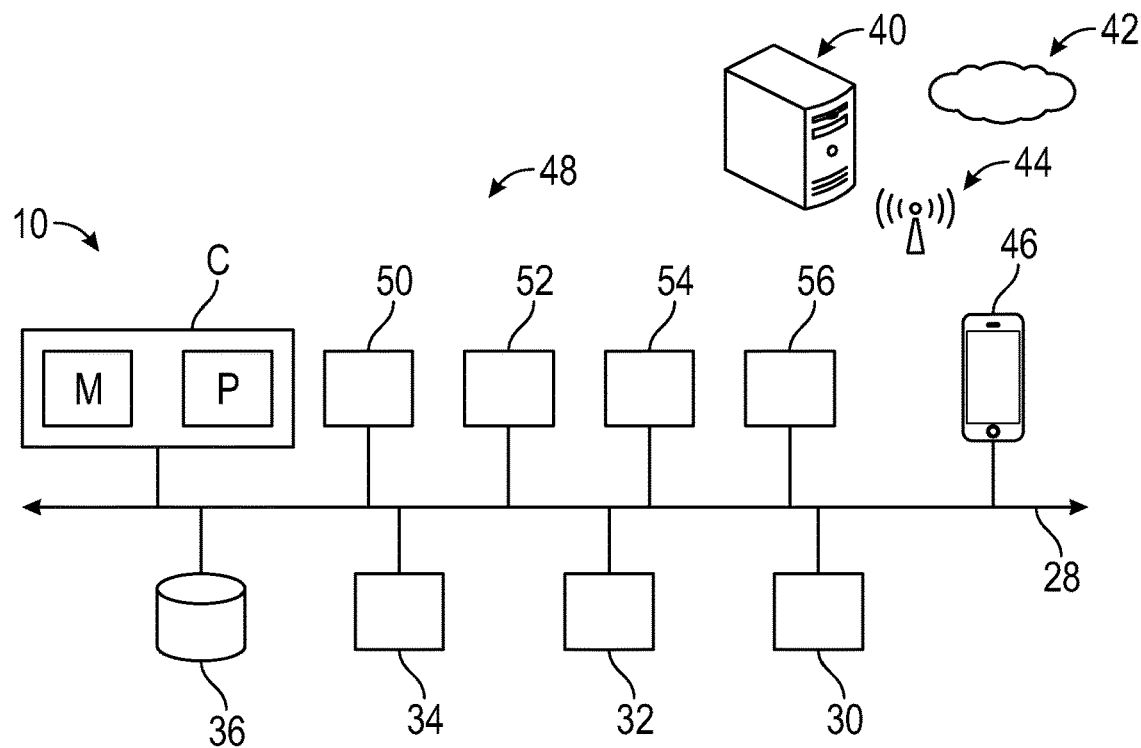
FIG. 1 is a schematic illustration of a system for selecting an intraocular lens for implantation into an eye, the system having a controller.
Figure 2:
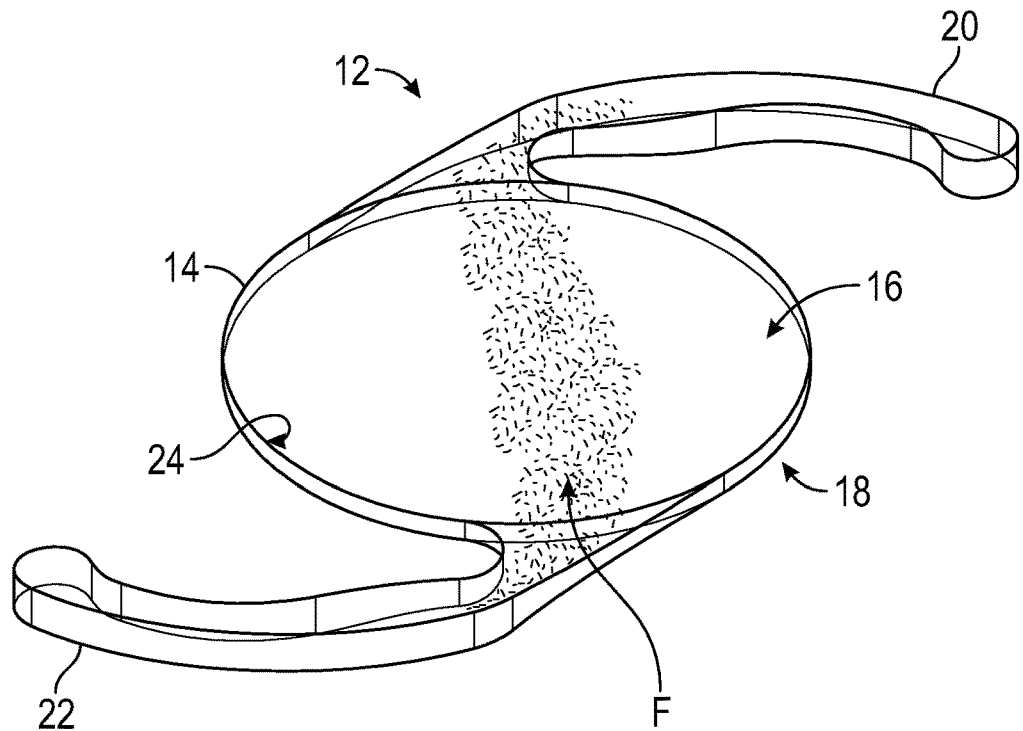
FIG. 2 is a schematic perspective view of an example intraocular lens.

Referring to the drawings, wherein like reference numbers refer to like components, FIG. 1 schematically illustrates a system 10 for selecting an intraocular lens for implantation. An example of an intraocular lens 12 is shown in FIG. 2. However, any type of intraocular lens available to those skilled in the art may be employed. The system 10 employs a robust, multi-prong approach utilizing a plurality of machine learning models. As described below, the system 10 leverages both rich image data and numerical data for optimizing the selection of the intraocular lens 12.

Referring to FIG. 2, the intraocular lens 12 includes an optic zone 14 defining a first surface 16 and a second surface 18. The optic zone 14 may be contiguous with one or more supporting structures, such as first supporting structure 20 and second supporting structure 22, which are configured to support positioning and retention of the intraocular lens 12. The intraocular lens 12 may define an internal cavity 24 at least partially filled with fluid F. The fluid F is configured to be movable within the internal cavity 24 in order to vary a thickness (and power) of the intraocular lens 12. It is to be understood that the intraocular lens 12 may take many different forms and include multiple and/or alternate components.

Figure 4:
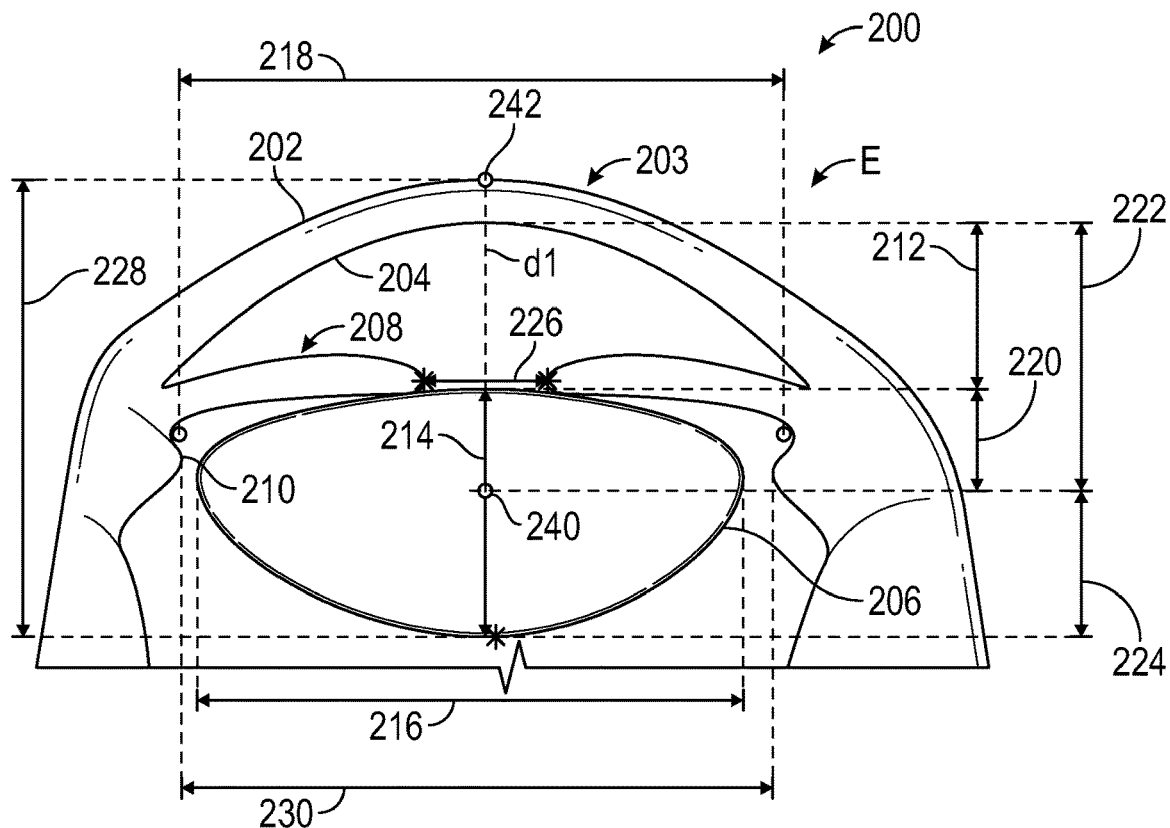
FIG. 4 is a schematic fragmentary cross-sectional view of an example pre-operative image of an eye.
Figure 5:
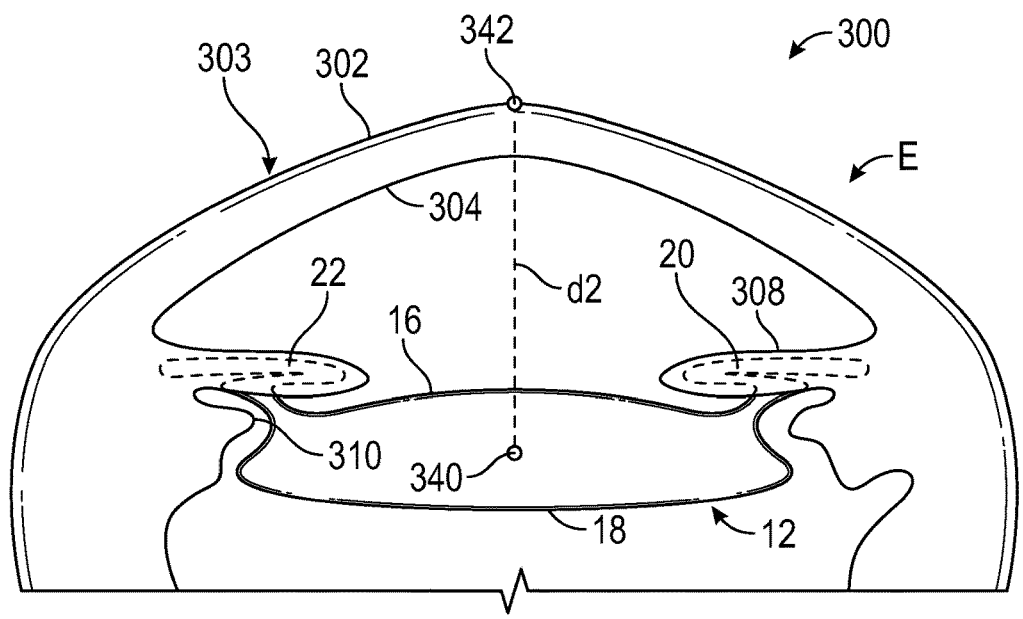
FIG. 5 is a schematic fragmentary cross-sectional view of an example post-operative image of an eye.

Referring to FIG. 1, the system 10 includes a controller C having at least one processor P and at least one memory M (or non-transitory, tangible computer readable storage medium) on which are recorded instructions for executing a method 100 for selecting the intraocular lens 12. Method 100 is shown in and described below with reference to FIG. 3. FIG. 4 shows an example pre-operative image 200 of an eye E. FIG. 5 shows an example post-operative image 300 of the eye E.

Referring now to FIG. 1, the controller C may be configured to communicate with various entities via a short-range network 28, such as for example, a first imaging device 30. The first imaging device 30 may be an ultrasound machine, a magnetic resonance imaging machine or other imaging device available to those skilled in the art. The short-range network 28 may be wireless or may include physical components. The short-range network 28 may be a bus implemented in various ways, such as for example, a serial communication bus in the form of a local area network. The local area network may include, but is not limited to a Controller Area Network (CAN), a Controller Area Network with Flexible Data Rate (CAN-FD), Ethernet, blue tooth, WIFI and other forms of data connection. The short-range network 28 may be a Bluetooth™ connection, defined as being a short-range radio technology (or wireless technology) aimed at simplifying communications among Internet devices and between devices and the Internet. Bluetooth™ is an open wireless technology standard for transmitting fixed and mobile electronic device data over short distances and creates personal networks operating within the 2.4 GHz band. Other types of connections may be employed.

Referring to FIG. 1, the controller C may be in communication with a second imaging device 32, a display module and/or user interface 34 and a database 36. Additionally, the controller C may be configured to communicate with a remote server 40 and/or a cloud unit 42, via a long-range network 44. The remote server 40 may be a private or public source of information maintained by an organization, such as for example, a research institute, a company, a university and/or a hospital. The cloud unit 42 may include one or more servers hosted on the Internet to store, manage, and process data. The long-range network 44 may be a Wireless Local Area Network (LAN) which links multiple devices using a wireless distribution method, a Wireless Metropolitan Area Networks (MAN) which connects several wireless LANs or a Wireless Wide Area Network (WAN) which covers large areas such as neighboring towns and cities. Other types of connections may be employed.

The controller C may be configured to receive and transmit wireless communication to the remote server 40 through a mobile application 46, shown in FIG. 1. The mobile application 46 may in communication with the controller C via the short-range network 28 such that it has access to the data in the controller C. In one example, the mobile application 46 is physically connected (e.g. wired) to the controller C. In another example, the mobile application 46 is embedded in the controller C. The circuitry and components of a remote server 40 and mobile application 46 ("apps") available to those skilled in the art may be employed.

The controller C is specifically programmed to selectively execute a plurality of machine learning models 48. The controller C may access the plurality of machine learning models 48 via the short-range network 28, the long-range network 44 and/or mobile application 46. Alternatively, the plurality of machine learning models 48 may be embedded in the controller C. The plurality of machine learning models 48 may be configured to find parameters, weights or a structure that minimizes a respective cost function. Each of the plurality of machine learning models 48 may be a respective regression model. In one example, referring to FIG. 1, the plurality of machine learning models 48 includes a first input machine learning model 50, a second input machine learning model 52, a third input machine learning model 54 and an output machine learning model 56.

The plurality of machine learning models 48 may include a neural network algorithm. As understood by those skilled in the art, neural networks are designed to recognize patterns and modeled loosely after the human brain. The patterns are recognized by the neural networks from real-world data (e.g. images, sound, text, time series and others) that is translated or converted into numerical form and embedded in vectors or matrices. The neural network may employ deep learning maps to match an input vector x to an output vector y. Stated differently, each of the plurality of machine learning models 48 learns an activation function $f$ such that $f(x)$ maps to y. The training process enables the neural network to correlate the appropriate activation function $f(x)$ for transforming the input vector x to the output vector y. In the case of a simple linear regression model, two parameters are learned: a bias and a slope. The bias is the level of the output vector y when the input vector x is 0 and the slope is the rate of predicted increase or decrease in the output vector y for each unit increase in the input vector x. Once the plurality of machine learning models 48 is respectively trained, estimated values of the output vector y may be computed with given new values of the input vector x.

Figure 6:
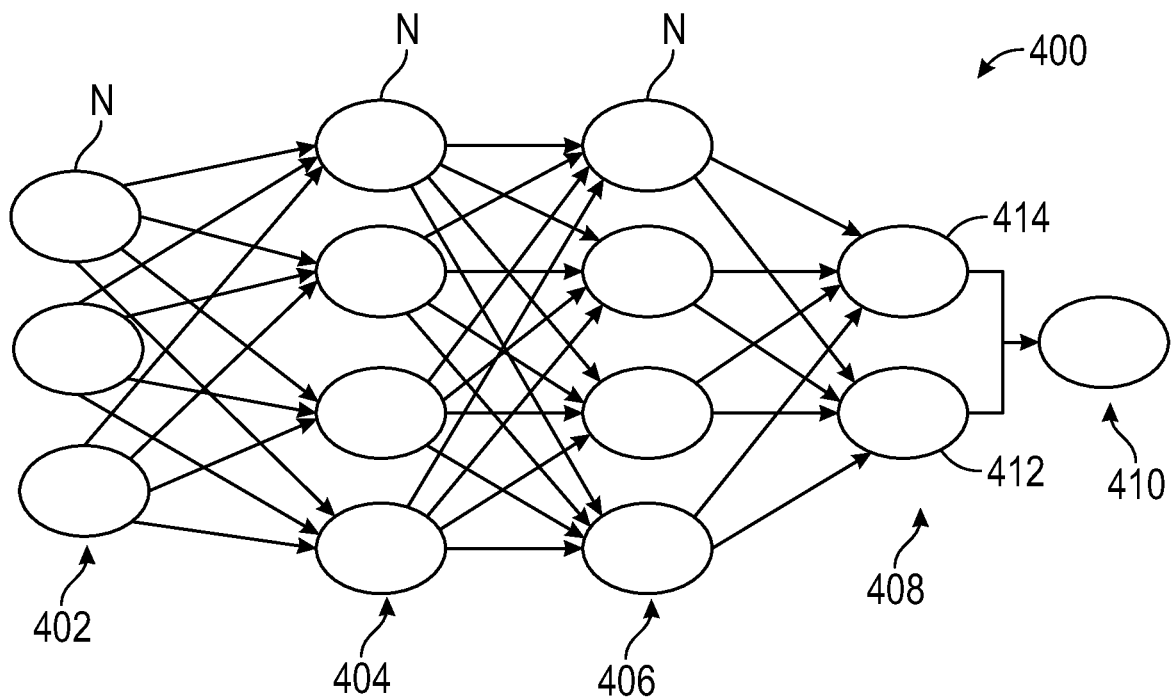
FIG. 6 is a schematic example of a multi-layer perceptron algorithm executable by the controller of FIG. 1.

The plurality of machine learning models 48 may include a multi-layer perceptron network. Referring to FIG. 6, an example of a multilayer perceptron network 400 is shown. The multilayer perceptron network 400 is a feedforward artificial neural network having at least three layers of nodes N, including an input layer 402, one or more hidden layers 408 (such as first hidden layer 404 and second hidden layer 406), and an output layer 410. Each of the layers is composed of nodes N configured to perform an affine transformation of a linear sum of inputs. The nodes N are neurons characterized by a respective bias and respective weighted links. The nodes N in the input layer 402 receive the input, normalize them and forward them to nodes N in the first hidden layer 404. Each node N in a subsequent layer computes a linear combination of the outputs of the previous layer. A network with three layers would form an activation function $f(x)=f(3)(f(2)(f(1)(x)))$. The activation function $f$ may be linear for the respective nodes N in the output layer 410. The activation function $f$ may be a sigmoid for the first hidden layer 404 and the second hidden layer 406. A linear combination of sigmoids is used to approximate a continuous function characterizing the output vector y. Other types of neural networks may be employed.

Figure 7:
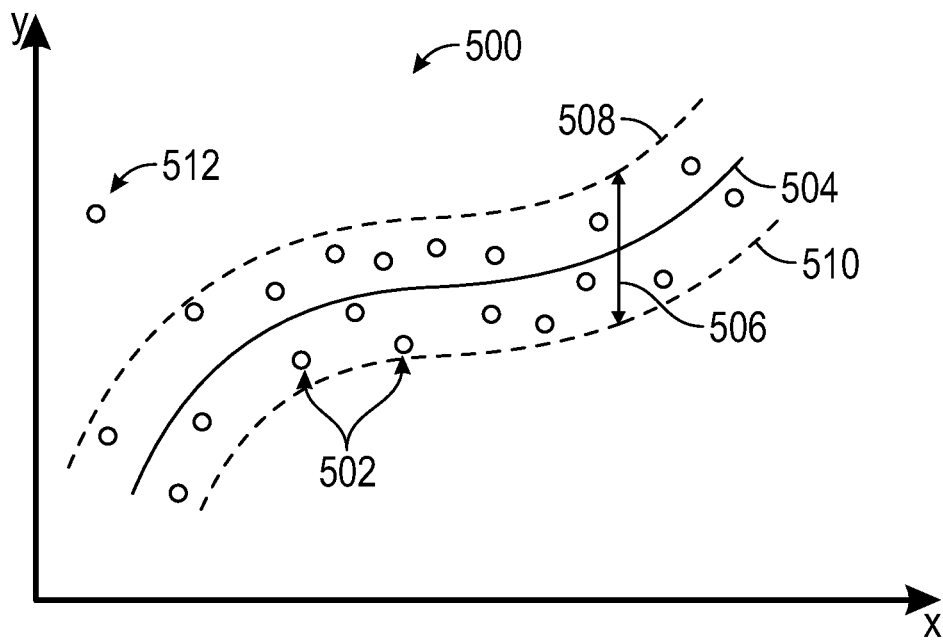
FIG. 7 is a schematic example of a support vector regression (SVR) technique by the controller of FIG. 1.

The plurality of machine learning models 48 may include a support vector regression (SVR) model. FIG. 7 shows an example of a support vector regression model 500 for data points 502. The support vector regression model 500 is configured to find a function (hyperplane 504 in FIG. 7) such that the data points 502 are within a margin 506 from this function, i.e., inside a first boundary line 508 and a second boundary line 510. Referring to FIG. 7, the hyperplane 504 may be defined as the line that will match the input vector x to the output vector y, i.e. predict a target value. The hyperplane 504 is individualized so as to maximize the margin 506 and minimize a predefined error. If there are points (such as extraneous point 512) that are outside the margin 506, a penalty may be built into the support vector regression model 500. Prior to ascertaining the hyperplane 504, the support vector regression model 500 may employ a kernel function to map a lower dimensional dataset into a higher dimensional dataset. Other machine learning models available to those skilled in the art may be employed.

Figure 3:
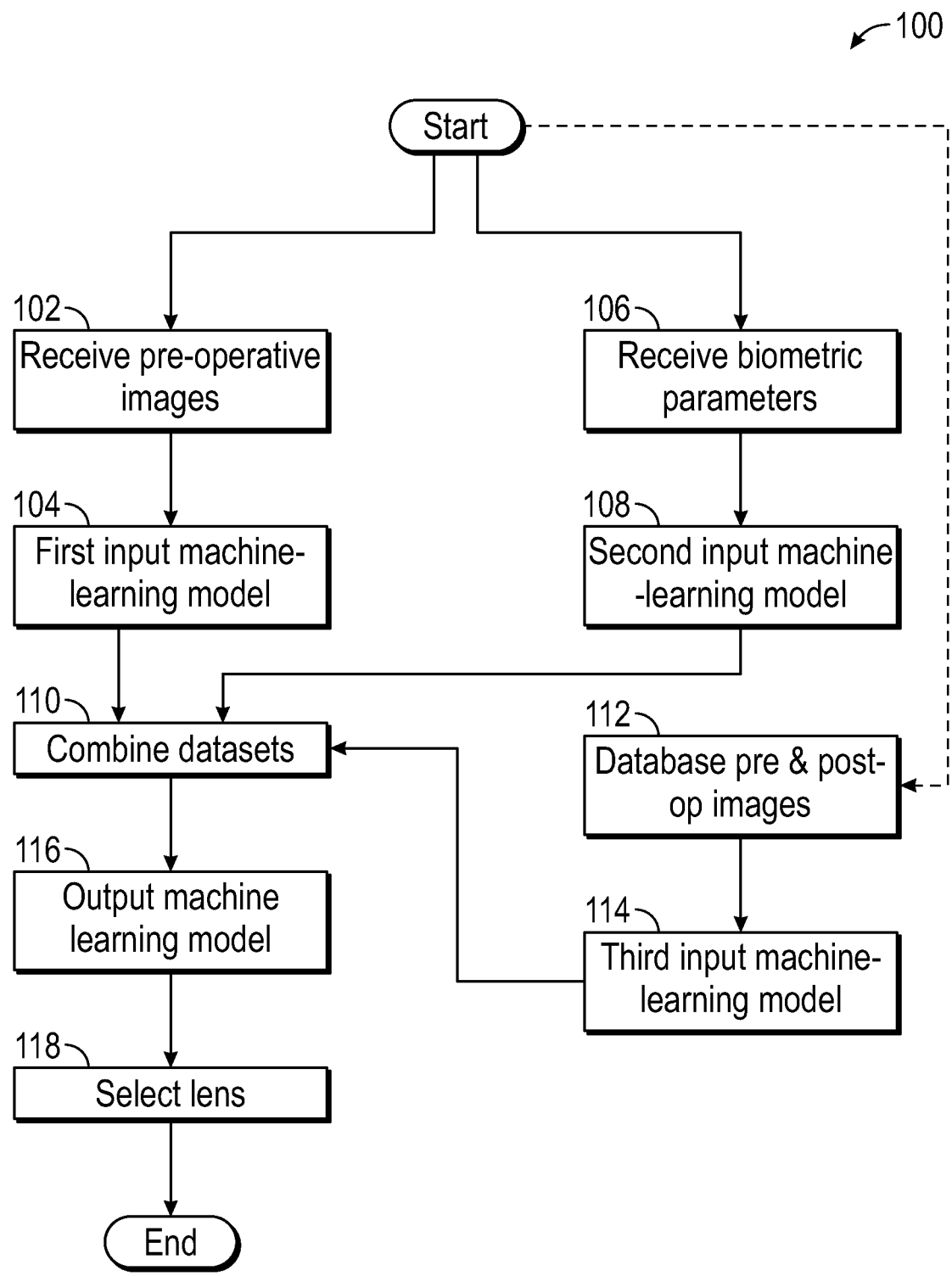
FIG. 3 is a schematic flowchart for a method executable by the controller of FIG. 1.

Referring now to FIG. 3, a flow chart of method 100 executable by the controller C of FIG. 1 is shown. Method 100 need not be applied in the specific order recited herein and some blocks may be omitted. The memory M can store controller-executable instruction sets, and the processor P can execute the controller-executable instruction sets stored in the memory M.

Per block 102 of FIG. 3, the controller C is configured to receive at least one pre-operative image of the eye. An example pre-operative image 200 of an eye E is shown in FIG. 4. FIG. 4 is not drawn to scale. FIG. 4 illustrates an upper surface 202 of the cornea 203, a lower surface 204 of the cornea 203, the pre-operative lens 206, iris 208 and ciliary muscle 210. The pre-operative image 200 may be obtained via an ultrasound bio-microscopy technique. The ultrasound bio-microscopy technique may employ a relatively high frequency transducer of between about 35 MHz and 100 MHz, with a depth of tissue penetration between about 4 mm and 5 mm. Other imaging modalities may be employed, including but not limited to, optical coherence tomography and magnetic resonance imaging. The plurality of machine learning models 48 may be trained using a single image or a series of images.

Per block 104 of FIG. 3, the method 100 includes extracting, via the first input machine learning model 50, a first set of data based in part on at least one pre-operative image, such as the example pre-operative image 200 shown in FIG. 4. The first set of data may be presented in the form of a three-dimensional matrix. This provides a technical advantage of leveraging the rich image data. Referring to FIG. 4, the first set of data may include a plurality of pre-operative dimensions such as an anterior chamber depth 212, a lens thickness 214, a lens diameter 216 and a sulcus-to-sulcus diameter 218. The plurality of pre-operative dimensions may include a first equatorial plane position 220 (measured from an anterior phakic pole), a second equatorial plane position 222 (measured relative to the anterior chamber depth 212) and a third equatorial plane position 224 (measured relative to a posterior phakic pole). Referring to FIG. 4, the plurality of pre-operative dimensions may further include an iris diameter 226, an axial length 228 from the cornea 203 to a posterior surface of the pre-operative lens 206 and a ciliary process diameter 230.

Per block 106 of FIG. 3, the controller C is configured to receive multiple biometric parameters, which may include pre-operative dimensions of the eye E, such as a K flat factor, a K steep factor and an average K factor. The multiple biometric parameters may further include an anterior chamber depth 212, a lens thickness 214, a lens diameter 216, a ciliary process diameter 230 and a sulcus-to-sulcus diameter 218. The multiple biometric parameters may further include parameters related to the intraocular lens 12, such as lens power and thickness. In one example, the pre-operative image 200 is obtained from a first imaging device 30 and the multiple biometric parameters are obtained from a second imaging device 32, with the second imaging device 32 being different from the first imaging device 30. For example, the first imaging device 30 may be an ultrasound device and the second imaging device 32 may be an optical coherence tomography device. It is to be understood that other imaging modalities may be employed. In another example, the pre-operative image 200 and the multiple biometric parameters are obtained from the same imaging modality.

Per block 108 of FIG. 3, the method 100 includes extracting, via the second input machine learning model 52, a second set of data based in part on the multiple biometric parameters. The second set of data may be presented in the form of a three-dimensional vector. Per block 110 of FIG. 3, the controller C is configured to combine the first set of data and the second set of data to obtain a mixed set of data.

Optionally, per block 112, the method 100 may include accessing historical pairs of respective pre-operative and post-operative images, such as the pre-operative image 200 and the post-operative image 300 shown in FIGS. 4 and 5, respectively. FIG. 5 illustrates the upper surface 302 of the cornea 303, the lower surface 304 of the cornea 303, the iris 308 and the ciliary muscle 310. Also shown in FIG. 5 is the implanted intraocular lens 12, the first surface 16, the second surface 18, the first supporting structure 20 and the second supporting structure 22. FIG. 5 is not drawn to scale. The post-operative image 300 may be obtained via an ultrasound bio-microscopy technique or other imaging modality available to those skilled in the art. Referring to FIG. 1, the controller C may be configured to obtain the historical pairs from the database 36 via the short-range network 28. The controller C may be configured to obtain the historical pairs from the remote server 40 via the long-range network 44.

Per block 114, the controller C is configured to extract, via the third input machine learning model 54, a third set of data based in part on a comparison of the historical pairs. The third set of data is added to the mixed set of data. In one example, the third input machine learning model 54 is a deep learning neural network configured to classify pre-operative measurements (x) in the pre-operative image 200 to determine a proposed lens power (f(x)) and subsequently determine an estimated error that may result from using the proposed intraocular lens power. The third input machine learning model 54 may be configured to minimize a cost function defined as the mean squared error between a predicted manifest refraction spherical equivalent (based on the pre-operative image 200) and a post-operative manifest refraction spherical equivalent (based on the post-operative image 300).

The comparison of the historical pairs may entail tracking changes in specific parameters between the pre-operative image 200 and post-operative image 300. For example, comparison may include assessing the difference between a first distance d1, shown in FIG. 4, and a second distance d2, shown in FIG. 5. The first distance d1 is between a center 240 of the pre-operative lens 206 and a reference point 242 on the upper surface 202 of the cornea 203 in the pre-operative image 200. The second distance d2 is between a center 340 of the intraocular lens 12 implanted and a reference point 342 on the upper surface 302 of the cornea 303 in the post-operative image 300. Other parameters may be employed.

Per block 116 of FIG. 3, the method 100 includes generating, via the output machine learning model 56, at least one output factor based on the mixed set of data. Referring to FIG. 6, the output machine learning model 56 may be a fully connected perceptron model such that the parameters of each node N are independent of others, i.e., each node N is characterized by a unique set of weights. Referring to FIG. 6, the output machine learning model 56 may generate multiple outputs, such as the first output factor 412 and the second output factor 414. The first output factor 412 may be a manifest refraction spherical equivalent (MRSE). The second output factor 414 may be an uncorrected distance visual acuity (UCDVA).

Optionally, prior to generating the output factor per block 116, the controller C may configured to obtain one or more imputed post-operative variables, based in part on the plurality of pre-operative dimensions. The imputed post-operative variables may include a post-operative lens thickness and post-operative lens position. The imputed post-operative variables are added to the mixed set of data and considered as an additional input to the output machine learning model 56 for generating the output factor in block 116. The imputed post-operative variables may be obtained from a geometric model or intraocular lens power calculation formula available to those skilled in the art, such as for example, the SRK/T formula, the Holladay formula, the Hoffer Q formula, the Olsen formula and the Haigis formula. The imputed post-operative variables may be obtained from other estimation methods available to those skilled in the art.

Per block 118 of FIG. 3, the method 100 includes selecting the intraocular lens 12 based in part on the at least one output factor generated in block 116. In the case of multiple output factors, the controller C may be configured to use a weighted average of the multiple output factors or other statistical methods (e.g. a neural net) to determine the correct power of the intraocular lens 12 to be implanted.

In summary, the system 10 and method 100 optimize the selection process for an intraocular lens 12 and enable a greater prediction success rate, particularly in eyes with irregular biometry. The system 10 and method 100 may be applied to a wide range of imaging modalities, both during the model training and the model execution process.

The controller C of FIG. 1 includes a computer-readable medium (also referred to as a processor-readable medium), including a non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random-access memory (DRAM), which may constitute a main memory. Such instructions may be transmitted by one or more transmission media, including coaxial cables, copper wire and fiber optics, including the wires that comprise a system bus coupled to a processor of a computer. Some forms of computer-readable media include, for example, a floppy disk, a flexible disk, hard disk, magnetic tape, other magnetic medium, a CD-ROM, DVD, other optical medium, punch cards, paper tape, other physical medium with patterns of holes, a RAM, a PROM, an EPROM, a FLASH-EEPROM, other memory chip or cartridge, or other medium from which a computer can read.

Look-up tables, databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store may be included within a computing device employing a computer operating system such as one of those mentioned above, and may be accessed via a network in one or more of a variety of manners. A file system may be accessible from a computer operating system, and may include files stored in various formats. An RDBMS may employ the Structured Query Language (SQL) in addition to a language for creating, storing, editing, and executing stored procedures, such as the PL/SQL language mentioned above.

The detailed description and the drawings or FIGS. are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. A system for selecting an intraocular lens for implantation into an eye, the system comprising:
a controller having a processor and tangible, non-transitory memory on which instructions are recorded;
wherein the controller is configured to selectively execute a plurality of machine learning models, including a first input machine learning model, a second input machine learning model and an output machine learning model;
wherein execution of the instructions by the processor causes the controller to:
receive at least one pre-operative image of the eye and extract, via the first input machine learning model, a first set of data based in part on the at least one pre-operative image;
receive multiple biometric parameters of the eye and extract, via the second input machine learning model, a second set of data based in part on the multiple biometric parameters;
combine the first set of data and the second set of data to obtain a mixed set of data;
generate, via the output machine learning model, at least one output factor based on the mixed set of data; and
select the intraocular lens based in part on the at least one output factor, wherein the intraocular lens includes an optic zone contiguous with one or more supporting structures; and the intraocular lens includes an internal cavity at least partially filled with a fluid, the fluid being configured to move within the internal cavity to vary a power of the intraocular lens.

2. The system of claim 1, wherein:
the at least one output factor is a manifest refraction spherical equivalent (MRSE).

3. The system of claim 1, wherein:
the at least one pre-operative image is obtained from a first imaging device and the multiple biometric parameters are obtained from a second imaging device, the first imaging device being different from the second imaging device.

4. The system of claim 1, wherein:
the plurality of machine learning models includes a third input machine learning model and prior to generating the at least one output factor, the controller is configured to:
access historical pairs of respective pre-operative and post-operative images;
extract, via the third input machine learning model, a third set of data based in part on the historical pairs; and
add the third set of data to the mixed set of data prior to generating the at least one output factor.

5. The system of claim 1, wherein:
the at least one pre-operative image is an ultrasound bio-microscopy image.

6. The system of claim 1, wherein:
each of the plurality of machine learning models is a respective regression model; and
the output machine learning model includes a multi-layer perceptron network.

7. The system of claim 1, wherein:
the multiple biometric parameters include a K flat factor and a K steep factor.

8. The system of claim 1, wherein:
the first set of data includes a plurality of pre-operative dimensions of the eye; and
the plurality of pre-operative dimensions includes one or more of an anterior chamber depth, a lens thickness, a lens diameter, a sulcus-to-sulcus diameter, a first equatorial plane position, a second equatorial plane position, a third equatorial plane position, an iris diameter, an axial length from a first surface of a cornea to a posterior surface of a pre-operative lens and a ciliary process diameter.

9. The system of claim 1, wherein prior to generating the at least one output factor, the controller is configured to:
obtain one or more imputed post-operative variables based in part on the plurality of pre-operative dimensions, the one or more imputed post-operative variables including a post-operative lens thickness and post-operative lens position; and
add the one or more imputed post-operative variables to the mixed set of data prior to generating the at least one output factor.

10. The system of claim 1, wherein:
the first set of data includes a plurality of pre-operative dimensions of the eye; and
the plurality of pre-operative dimensions includes each of an anterior chamber depth, a lens thickness, a lens diameter, a sulcus-to-sulcus diameter, an iris diameter, an axial length from a first surface of a cornea to a posterior surface of a pre-operative lens, a ciliary process diameter, a first equatorial plane position, a second equatorial plane position and a third equatorial plane position.

11. A method of selecting an intraocular lens for implantation in an eye, the method comprising:
receiving, via a controller having a processor and tangible, non-transitory memory, at least one pre-operative image of the eye;
selectively executing a plurality of machine learning models, via the controller, the plurality of machine learning models including a first input machine learning model, a second input machine learning model and an output machine learning model;
extracting, via the first input machine learning model, a first set of data based in part on the at least one pre-operative image;
receiving, via the controller, multiple biometric parameters of the eye;
extracting, via the second input machine learning model, a second set of data based in part on the multiple biometric parameters;
combining, via the controller, the first set of data and the second set of data to obtain a mixed set of data;
generating, via the output machine learning model, at least one output factor based on the mixed set of data; and
selecting the intraocular lens based in part on the at least one output factor, wherein the intraocular lens includes an optic zone contiguous with one or more supporting structures; and the intraocular lens includes an internal cavity at least partially filled with a fluid, the fluid being configured to move within the internal cavity to vary a power of the intraocular lens.

12. The method of claim 11, further comprising, prior to generating the at least one output factor:
accessing, via the controller, historical pairs of respective pre-operative and post-operative images;
including a third input machine learning model in the plurality of machine learning models;
extracting, via the third input machine learning model, a third set of data based in part on a comparison of the historical pairs; and
adding the third set of data to the mixed set of data prior to generating the at least one output factor.

13. The method of claim 11, wherein:
each of the plurality of machine learning models is a respective regression model; and
the output machine learning model includes a multi-layer perceptron network.

14. The method of claim 11, wherein:
the multiple biometric parameters include a K flat factor and a K steep factor.

15. The method of claim 11, wherein:
the first set of data includes a plurality of pre-operative dimensions of the eye; and
the plurality of pre-operative dimensions includes one or more of an anterior chamber depth, a lens thickness, a lens diameter, a sulcus-to-sulcus diameter, a first equatorial plane position, a second equatorial plane position, a third equatorial plane position, an iris diameter, an axial length from a first surface of a cornea to a posterior surface of a pre-operative lens and a ciliary process diameter.

16. The method of claim 11, wherein:
the first set of data includes a plurality of pre-operative dimensions of the eye; and
the plurality of pre-operative dimensions includes each of an anterior chamber depth, a lens thickness, a lens diameter, a sulcus-to-sulcus diameter, an iris diameter, an axial length from a first surface of a cornea to a posterior surface of a pre-operative lens and a ciliary process diameter.

17. The method of claim 11, further comprising:
obtaining the at least one pre-operative image from a first imaging device and obtaining the multiple biometric parameters from a second imaging device, the first imaging device being different from the second imaging device.

18. A system for selecting an intraocular lens for implantation into an eye, the system comprising:
  a controller having a processor and tangible, non-transitory memory on which instructions are recorded;
  wherein the controller is configured to selectively execute a plurality of machine learning models, including a first input machine learning model, a second input machine learning model, a third input machine learning model and an output machine learning model;
  wherein execution of the instructions by the processor causes the controller to:
    receive at least one pre-operative image of the eye and extract, via the first input machine learning model, a first set of data based in part on the at least one pre-operative image;
    receive multiple biometric parameters of the eye and extract, via the second input machine learning model, a second set of data based in part on the multiple biometric parameters;
    access historical pairs of respective pre-operative and post-operative images and extract, via the third input machine learning model, a third set of data based in part on the historical pairs;
    combine the first set of data, the second set of data and the third set of data to obtain a mixed set of data;
    generate, via the output machine learning model, at least one output factor based on the mixed set of data; and
    select the intraocular lens based in part on the at least one output factor; and
  wherein the at least one pre-operative image is obtained from a first imaging device and the multiple biometric parameters are obtained from a second imaging device, the first imaging device being different from the second imaging device, wherein the intraocular lens includes an optic zone contiguous with one or more supporting structures; and the intraocular lens includes an internal cavity at least partially filled with a fluid, the fluid being configured to move within the internal cavity to vary a power of the intraocular lens.

* * * * *